United States Patent [19]

Ishida et al.

US005179227A

[11] Patent Number: 5,179,227

[45] Date of Patent: Jan. 12, 1993

[54] FRACTIONATION PROCESS OF REACTION MIXTURE CONTAINING METHYLENE BRIDGED POLYPHENYLENE POLYISOCYANATE

[75] Inventors: Noritoshi Ishida, Fukuoka; Zunzi Tashima, Ohmuta; Mitsunori Shimamatsu, Fukuoka; Kazunari Nitta, Ohmuta; Takashi Nagou, Yokohama, all of Japan

[73] Assignee: Mitsui Toatsu Chemicals Inc., Tokyo, Japan

[21] Appl. No.: 779,733

[22] Filed: Oct. 23, 1991

[30] Foreign Application Priority Data

Oct. 23, 1990 [JP] Japan .................................. 2-283515

[51] Int. Cl.$^5$ ............................................ C07C 263/20
[52] U.S. Cl. .................... 560/352; 560/347; 560/359
[58] Field of Search ................ 560/352, 359, 347

[56] References Cited

U.S. PATENT DOCUMENTS

| | | | |
|---|---|---|---|
| 4,014,914 | 3/1977 | Pistor et al. | 560/347 |
| 4,128,569 | 12/1978 | Horn et al. | 560/347 |
| 4,847,408 | 7/1989 | Frosch et al. | 560/347 |

FOREIGN PATENT DOCUMENTS 58-26337  6/1983  Japan .

*Primary Examiner*—Joseé G. Dees
*Assistant Examiner*—Vera C. Clarke
*Attorney, Agent, or Firm*—Millen, White, Zelano and Branigan

[57] ABSTRACT

A fractionation process of a methylene bridged polyphenylene polyisocyanate mixture obtained by phosgenating condensation product of aniline and formaldehyde is disclosed.

In order to apply the above mixture to a variety of uses, the process separates the mixture into fractions by giving primary attention to the content of 4,4'-and 2,4'-isomer of diphenylmethane diisocyanate and at the same time reduces the content of impurities having acidity and hydrolyzable chlorine.

8 Claims, No Drawings

FRACTIONATION PROCESS OF REACTION MIXTURE CONTAINING METHYLENE BRIDGED POLYPHENYLENE POLYISOCYANATE

BACKGROUND OF THE INVENTION

1. Field of the Invention

The present invention relates to a process of the preparation of methylene bridged polyphenylene polyisocyante, and particularly relates to a fractionation process of a reaction mixture containing the polyisocyanate.

Methylene bridged polyphenylene polyisocyanate is a very reactive compound and widely utilized for polyurethane products such as foams, elastomers, adhesives and paints.

The present invention can conduct various modes of fractionation on methylene bridged polyphenylene polyisocyanate having the above many uses depending upon the kind and purity of the polyisocyanate and the variety and amount of impurities The above reaction product can hence be fractionated so as to obtain reaction materials which satisfy properties required for specific uses.

2. Disclosure of the Related Art

Methylene bridge polyphenylene polyisocyanate is prepared by phosgenating a polyamine mixture formed by condensation of aniline and formaldehyde. The product contains various kinds of diphenylmethane diisocyanate (hereinafter referred to as MDI) and can provide by distillation an isomer mixture of 2,4'-diphenylmethane diisocyanate (hereinafter referred to as 2,4'-MDI) and 4,4'-diphenylmethane diisocyanate (hereinafter referred to as 4,4'-MDI).

The residue obtained by the distillation also has various uses and thus preparations are generally made so as to suitable for the uses by mixing these fractionated products in an adequate proportion. However, phosgenation in preparing the MDI mixture inevitably generates impurities having acidity and hydrolyzable chlorine. These impurities have been known to lower the reactivity of the isocyanate group in the preparation of polyurethane products.

Conventionally known processes for reducing the acidity and hydrolyzable chlorine (hereinafter referred to as HC) contents are based on the treatment of the MDI mixture with an organometallic compound at high temperature. These processes, however, are not satisfactory because the organometallic compound is required in a large amount, remains in the product and leads to formation of tarry materials in the high temperature treatment.

On the other hand, separation processes by distillation, extraction and crystallization, respectively, have been conventionally known for the separation of the MDI isomer mixture. The separation process by distillation causes polymerization of isocyanate due to heating and decreases the yield of 4,4'-MDI. The separation process by extraction has a disadvantage of requiring solvent removal. The separation process by crystallization divides the isomer mixture into a mother liquor and a crystalline product and affords 4,4'-MDI as a high purity crystal. The process, however, cannot sufficiently reduce the acidity and HC content of the resulting 4,4'-MDI.

SUMMARY OF THE INVENTION

The basic invention is a process for fractionating a reaction mixture obtained by phosgenating a polyamine mixture resulting from the condensation of aniline and formaldehyde, said reaction mixture containing 4,4'-diphenylmethane diisocyanate as a primary component and 2,4'-diphenylmethane diisocyanate as a secondary component in the presence of impurities having acidity and hydrolyzable chlorine, comprising the steps of:

(A) distilling the reaction mixture to separate into a distillate (the first fraction) and a residue (the second fraction), (B) cooling the first fraction to precipitate a solid in an amount of not more than 85% by weight of the first fraction and successively removing the solid to obtain the third fraction, and (C) heat-treating the third fraction in an inert gas at 80° to 120° C. and removing a resultant gaseous portion at conventional pressure to obtain a liquid portion as the fourth fraction.

Prior to completing the present invention, the inventors found that the impurities having acidity and HC in the reaction mixture obtained by phosgenating the polyamine mixture defined herein can be roughly divided into two groups which have a lower boiling point and a higher boiling point than MDI, that the impurities having a large influence on the reactivity in the preparation of polyurethane products have the lower boiling point, that any impurities having acidity and HC are retained in the mother liquor in the crystallization step of MDI, and that these impurities can be decomposed by relatively mild heating and release hydrogen chloride gas.

The inventors can on the basis of these discoveries, simultaneously obtain a highly reactive MDI mixture having a low level of acidity and HC and high purity 4,4'-diphenylmethane diisocyanate. They also most efficiently can leave acidity and HC in the mother liquor by suitably selecting the MDI crystallization conditions. The purity of the 4,4'-diphenylmethane diisocyanate thus obtained is 98.5% or more.

DETAILED DESCRIPTION OF THE PREFERRED EMBODIMENT

The term "reaction mixture" refers to a mixture of crude methylene bridged polyphenylene polyisocyanate obtained by phosgenating a polyamine mixture resulting from condensation of aniline and formaldehyde in the presence of an acid catalyst. The mixture contains 2,4'-MDI and 4,4'-MDI in a proportion of 1:99 to 15:85. The sum of the 2,4'- and 4,4'-MDI is 40 to 80% of the mixture. The mixture additionally contains various polynuclear isocyanate compounds and impurities having 0.01 to 0.05% of acidity and 0.1 to 0.5% of HC which are particular problems in the invention.

The composition of the MDI mixture depends upon the composition of polyamine mixture and the composition of the polyamine mixture is affected by the aniline/hydrochloric/formaldehyde ratios in the condensation reaction. Phosgenation of the polyamine mixture may be carried out continuously or batchwise under atmospheric or increased pressure.

The distillation in step (A), i.e., the separation of the first and the second fraction by distillation of the crude polyisocyanate, can be carried out by batch operation with simple distillation equipment or by continuous operation with thin film distillation equipment. In order to prevent polymerization of isocyanate by heat, the distillation is carried out using the thin film distillation equipment under reduced pressure of usually 0.2 to 10 mmHg, preferably 0.5 to 5 mmHg, more preferably 1.0 to 3.0 mmHg and at a temperature of usually 180° to 250° C., preferably 180° to 230° C., more preferably 180° to 200° C.

The distillate is cooled into a liquid to form the first fraction. In order to avoid formation of dimer, it is preferred to cool the distillate quickly to 100° C. The proportion of the first fraction to the second fraction can be optionally changed. The isomer ratio of 2,4'-MDI to 4,4'MDI in the first fraction is affected by the composition of the polyamine mixture.

MDI still remains in the second fraction in a proportion of 20 to 50% and the major part is a mixture of polynuclear isocyanates. The second fraction also contains 0.02 to 0.06% acidity and 0.15 to 0.50% HC.

The first fraction is cooled in step (B), i.e., the crystallization step, to into an uncrystallized portion (the third fraction) and a crystallized product. In this step, the temperature is controlled in such a way that the amount of the crystallized product is 85% by weight or less of the first fraction.

The third fraction contains 2,4'-MDI and 4,4'-MDI in a ratio of 5:95 to 30:70 and also contains 0.03 to 0.06% of acidity and 0.05 to 0.1% of HC.

The third fraction is heat-treated in step (C). The treatment is readily carried out by using a reactor equipped with a heating jacket and an inert gas inlet tube and heat-treating the fraction at 80° to 120° C. while feeding the inert gas. The acid gas containing inert gas which evolves is usually removed from the system and may be recycled to the system after suitable neutralization and drying. The inert gases which can be used for the heat-treatment include nitrogen, helium, argon, carbon monoxide and carbon dioxide. Nitrogen is preferred in view of economy. The amount of the inert gas differs depending upon the treating time. For a treatment time of 2 hours, the preferred amount of the inert gas is 0.01 to 1.0 part by weight per hour per part by weight of the formed product. A treating temperature lower than 80° C. does not appreciably decompose acidity and HC. When the temperature is higher than 120° C., the decomposition of acidity and HC progresses whereas formation of the dimer unfavorably increases. The heating procedure can lower acidity and HC to about one tenth of the amount before treatment.

The third fraction thus heat-treated separates into a gaseous fraction at ordinary temperature and pressure to yield a liquid portion as the fourth fraction which contains decreased amount of acidity and HC. The thus-obtained fourth fraction can be blended with the second fraction in an optional proportion to produce a preparation having an MDI content or viscosity which conforms to respective use. The preparation obtained by mixing the second and the fourth fractions has acidity of 0.005 to 0.02% and HC of 0.05 to 0.15%, which can be varied by the mixing ratio. Hence, the thus-obtained preparation exhibits higher reactivity as compared with the preparation obtained by using the third fraction without heat-treatment.

In the next step, the solid obtained in step (B) can be divided by gradual warming into an initially molten portion (the fifth fraction) and principally molten portion (the sixth fraction).

For example, the solid is gradually warmed to 40° C. to obtain the fifth fraction as a liquid product. The residual solid is further warmed to about 55° C. to obtain the sixth fraction in the form of a molten product. It is preferred for maintaining high purity of the fifth fraction to increase the temperature to 40° C. as slowly as possible. This is because the solid itself is a mixture of crystalline materials. The term "as slowly as possible" is a matter of degree. For example, the solid obtained in step of (B) is gradually warmed over about 5 hours from the temperature of the solid itself to 40° C.

The fifth fraction obtained by an ideal treatment is a mixture composed of 2.0 to 7.0% of 2,4'-MDI, 93.0 to 98.0% of 4,4'-MDI, 0.005 to 0.020% of acidity and 0.01 to 0.05% of HC. The fraction is very valuable for the raw materials of liquid MDI and modified polyurethanes.

The sixth fraction is high purity 4,4'-MDI which contains only 1.5% or less of 2,4'-MDI, 0.001 to 0.003% of acidity and 0.002 to 0.005% of HC. It is better to use the intact fraction rather than further separating the two ingredients. The sixth fraction can be used without any problem as high purity 4,4'-MDI for the raw material of various polyurethane products.

The isomer ratio of MDI in each fraction mentioned above can be varied by controlling cooling temperature, warming temperature and speed of cooling or warming.

In order to obtain high purity 4,4'-MDI having low impurity content or to obtain the third fraction by efficiently concentrating impurities, the preferred yield ratio for the thus-divided fractions is, for example, 100 in the first fraction, 10 to 40 in the third fraction, 10 to 40 in the fifth fraction, and 40 to 60 in the sixth fraction.

EXAMPLE 1

A mixture of 2.46 kg (25.1 moles) of aniline (95 wt %, purity), 0.81 kg of formalin (10 moles of formaldehyde) and 1.64 kg (11.2 moles) of 25% hydrochloric acid was heated at an elevating temperature range of 30° C. to 120° C. for 3 hours. Into a 1.78 kg of the reaction mixture, 8.72 kg (88 moles) of phosgene was introduced at an elevating temperature range of 10° C. to 140° C. over 3 hours to obtain 11.3 kg of crude methylene-bridged polyphenylene polyisocyanate mixture. The mixture contained 3% of 2,4'-MDI, 60% of 4,4'-MDI, 0.015% of acidity, and 0.15% of HC. The mixture was distilled by using thin-film distillation equipment at 210° to 220° C. under a pressure of 2 mmHg to obtain 40% of the first fraction and 60% of the second fraction.

The first fraction was maintained in the liquid state at 36° C., transferred to a crystallizer and cooled to 24° C. over 8 hours. The first fraction was thus separated into 80% of crystallized portion and 20% of an uncrystallized portion (the third fraction).

The third fraction was treated by heating at 100° C. for 2 hours while introducing nitrogen in an amount of 0.5 part by weight per hour per part by weight of the product, thereby obtaining the fourth fraction which is liquid at ordinary temperature and pressure.

The fourth fraction and the second fraction were mixed in a proportion of 20:80 (referred to as 4-2 fraction).

The crystallized portion was warmed to 40° C. over about 5 hours and an initially molten portion (the fifth fraction) was separated in an amount of 20% of the first fraction. The remained portion was further warmed to 55° C. to separate the sixth fraction in the form of a molten material in an amount of 60% of the first fraction.

Analytical values of each fraction are illustrated in Table 1.

TABLE 1

| Fraction | MDI content (%) 2,4'- | MDI content (%) 4,4'- | Acidity (%) | HC (%) | Curing time*) (min) |
|---|---|---|---|---|---|
| 1 | 5.3 | 94.7 | 0.013 | 0.018 | 24 hrs< |
| 2 | 1.5 | 36.9 | 0.020 | 0.205 | 55.0 |
| 3 | 17.2 | 82.8 | 0.041 | 0.061 | 24 hrs< |
| 5 | 5.4 | 94.6 | 0.015 | 0.017 | 15.0 |
| 6 | 1.3 | 98.7 | 0.003 | 0.004 | 0.5 |
| 4 | 17.2 | 82.8 | 0.008 | 0.010 | 2.0 |
| 4-2 | 4.6 | 46.1 | 0.018 | 0.166 | 28.0 |

*)A mixture of 75 parts by weight of isocyanate, 25 parts by weight of xylene and 100 parts by weight of benzyl phenolic resin was prepared and curing time was measured.

EXAMPLE 2

The first fraction in Example 1 was cooled to 30° C. over 8 hours, and 70% of a crystallized portion and 30% of an uncrystallized portion (the third fraction) were obtained. Successively the crystallized portion was warmed to 40° C. over about 5 hours and 15% of a molten liquid (the fifth fraction) was separated. The residual solid portion was further warmed to 55° C. to obtain 55% of molten liquid as the sixth fraction.

The third fraction was treated by heating at 95° C. for 2 hours while introducing nitrogen in an amount of 0.5 part by weight per hour per part by weight of the product, thereby the fourth fraction which was liquid at conventional temperature and pressure was obtained. The fourth fraction was mixed with the second fraction of Example 1 in a proportion of 20:80 to obtain the 4-2 fraction.

Analytical values of each fraction are illustrated in Table 2.

TABLE 2

| Fraction | MDI content (%) 2,4'- | MDI content (%) 4,4'- | Acidity (%) | HC (%) | Curing time (min) |
|---|---|---|---|---|---|
| 3 | 13.3 | 86.7 | 0.033 | 0.050 | 24 hrs< |
| 5 | 4.8 | 95.2 | 0.012 | 0.013 | 10.5 |
| 6 | 1.1 | 98.9 | 0.002 | 0.002 | 0.5 |
| 4 | 13.3 | 86.7 | 0.005 | 0.007 | 1.5 |
| 4-2 | 3.9 | 46.9 | 0.017 | 0.158 | 26.0 |

EXAMPLE 3

The first fraction in Example 1 was cooled to 20° C. over 8 hours, and 85% of a crystallized portion and 15% of an uncrystallized portion (the third fraction) were obtained. Successively the crystallized portion was warmed to 40° C. over about 5 hours and 27% of molten liquid (the fifth fraction) was separated therefrom. The residual solid portion was further warmed to 55° C. to obtain 58% of molten liquid as the sixth fraction.

The third fraction was treated by heating at 105° C. for 2 hours while introducing nitrogen in an amount of 0.5 part by weight per hour per part by weight of the product, thereby obtaining the fourth fraction which was liquid at ordinary temperature and pressure. The fourth fraction was mixed with the second fraction of Example 1 in a proportion of 20:80 to obtain the 4-2 fraction.

Analytical values of each fraction are illustrated in Table 3

TABLE 3

| Fraction | MDI content (%) 2,4'- | MDI content (%) 4,4'- | Acidity (%) | HC (%) | Curing time (min) |
|---|---|---|---|---|---|
| 3 | 21.9 | 78.1 | 0.048 | 0.078 | 24 hrs< |
| 5 | 5.1 | 94.9 | 0.017 | 0.019 | 28.5 |
| 6 | 1.1 | 98.9 | 0.002 | 0.002 | 0.5 |
| 4 | 21.9 | 78.1 | 0.010 | 0.012 | 3.5 |
| 4-2 | 5.6 | 45.1 | 0.018 | 0.167 | 35.0 |

COMPARATIVE EXAMPLE 1

The first fraction in Example 1 was cooled to 24° C. over 8 hours, and 80% of a crystallized portion and 20% of an uncrystallized portion (the third fraction) were obtained. Successively the crystallized portion was warmed to 30° C. over about 5 hours and 10% of a molten liquid (the fifth fraction) was separated. The residual solid portion was further warmed to 55° C. to obtain 70% of molten liquid as the sixth fraction.

The third fraction was mixed intact with the second fraction of Example 1 in a proportion of 20:80 to obtain the 4-2 fraction.

Analytical values of each fraction are illustrated in Table 4.

TABLE 4

| Fraction | MDI content (%) 2,4'- | MDI content (%) 4,4'- | Acidity (%) | HC (%) | Curing time (min) |
|---|---|---|---|---|---|
| 3 | 17.2 | 82.8 | 0.041 | 0.061 | 24 hrs< |
| 5 | 5.5 | 94.5 | 0.016 | 0.018 | 30.0 |
| 6 | 1.9 | 98.1 | 0.005 | 0.006 | 5.5 |
| 4-2 | 4.6 | 46.1 | 0.024 | 0.176 | 350.0 |

What is claimed is:

1. A process for fractionating a reaction mixture obtained by phosgenating a polyamine mixture resulting from condensation of aniline and formaldehyde, said reaction mixture containing 4,4'-diphenylmethane diisocyanate as a primary component, 2,4'-diphenylmethane diisocyanate as a secondary component, impurities having acidity and hydrolyzable chlorine, comprising the steps of:

(A) distilling the reaction mixture into a distillate first fraction and a residue second fraction at a temperature of 180° to 250° C. and a pressure of 0.2 to 10 mmHg, (B) cooling the first fraction to precipitate therefrom a solid in an amount of not more than 85% by weight of the first fraction, (C) removing the precipitated solid to obtain a liquid third fraction and a solid third fraction, and either (D$_1$) heat-treating the liquid third fraction in an inert gas at 80° to 120° C. and removing a resultant gaseous portion at ambient temperature and pressure to obtain a liquid fourth fraction, or (D$_2$) warming the solid third fraction to a temperature not higher than 40° C. and removing the molten portion to obtain high purity 4,4'-diphenylmethane diisocyanate, or (D$_3$) conducting both (D$_1$) and D$_2$).

2. The process of claim 1 wherein steps (A) and (B) are conducted so as to yield from 15 to 40 parts by weight of the third liquid fraction from 100 parts by weight of the first fraction.

3. The process according to claim 1, comprising step (D$_1$).

4. The process according to claim 1, comprising the further step of mixing the liquid fourth fraction with the residue second fraction to obtain a diphenylemethane diisocyanate mixture having improved reactivity.

5. The process according to claim 1, comprising step (D$_2$).

6. The process according to claim 1, wherein step (A) is conducted by thin film distillation.

7. The process according to claim 6, wherein the temperature is 180°–250° C. and the pressure is 1.0–3.0 mm Hg.

8. The process according to claim 1, wherein in step (B) the first fraction is quickly cooled to 100° C.

* * * * *